(12) United States Patent
Yoon et al.

(10) Patent No.: US 7,122,527 B2
(45) Date of Patent: Oct. 17, 2006

(54) USE OF ANTISENSE OLIGONUCLEOTIDES TO INHIBIT THE EXPRESSION OF HUMAN AKT-1

(75) Inventors: Heejeong Yoon, Germantown, MD (US); Lingjun Mao, Hope, RI (US); Young Bok Lee, Rockville, MD (US); Chang Ho Ahn, Potomac, MD (US)

(73) Assignee: Rexahn Corporation, Potomac, MD (US)

( * ) Notice: Subject to any disclaimer, the term of this patent is extended or adjusted under 35 U.S.C. 154(b) by 547 days.

(21) Appl. No.: 10/640,167

(22) Filed: Aug. 13, 2003

(65) Prior Publication Data

US 2004/0265999 A1  Dec. 30, 2004

Related U.S. Application Data

(60) Provisional application No. 60/404,010, filed on Aug. 16, 2002.

(51) Int. Cl.
*A61K 31/70* (2006.01)
*C12N 5/00* (2006.01)
*C07H 21/04* (2006.01)
*C07H 21/02* (2006.01)
*C12Q 1/68* (2006.01)

(52) U.S. Cl. .................. 514/44; 435/375; 435/377; 435/6; 536/23.1; 536/24.1; 536/24.5

(58) Field of Classification Search ............... None
See application file for complete search history.

(56) References Cited

U.S. PATENT DOCUMENTS

5,958,773 A   9/1999   Monia et al.

OTHER PUBLICATIONS

Agrawal, Antisense Oligonucleotides: towards clinical trials 1996 Trends Biotechnol. 14: 376-387.
Brazil and Hemmings, Ten years of protein kinas B signalling: a hard Akt to follow 2001 Trends Biochem. Sci. 26: 657-664.
Crooke and Bennett, Progress in Antisense Oligonucleotide Therapeutics 1996 Annu. Rev. Pharmacol. Toxicol. 36:107-29.
Krieg, et al., CpG motifs in bacterial DNA trigger direct B-cell activation 1995 Nature 374: 546-549.
Laptev et al., Specific Inhibition of Expression of a Human Collagen Gene (COLIAI) with Modified Antisense Oligonucleotides. The Most Effective Target Sites are Clustered in Double-Stranded Regions of the Predicted Secondary Structure for the mRNA 1994 Biochemistry 33: 11033-11039.
Stocker, et al., Living with Lethal PIP3 levels: Viability of Flies Lacking PTEN Restored by a PH Domain Mutation in Akt/PKB Science, 2002, 295: 2088.
Martin, et al., Ein neuer Zugand zu 2'-0-Alkylribonucleosiden und Eigenschaften deren Oligonucleotide, Helv. Chim. Acta, 1995, 78: 486-504.
Chomczynski, P., and Sacchi, N., Single-Step Method of RNA Isolation by Acid Guanidinum Thiocyanate-Phenol-Chloroform Extraction, Anal. Biochem., 1987, 162: 156-159.
Skehan et al., New Colorimetric Cytotoxicity Assay for Anticancer-Drug Screening, J. National Cancer Institute, 1990, 82: 1107-1112.

*Primary Examiner*—Sean McGarry
(74) *Attorney, Agent, or Firm*—Valerie E. Looper

(57) ABSTRACT

New antisense oligonucleotide compounds inhibit expression of Akt-1 and also induce cytotoxicity in several cancer cell lines.

20 Claims, 12 Drawing Sheets

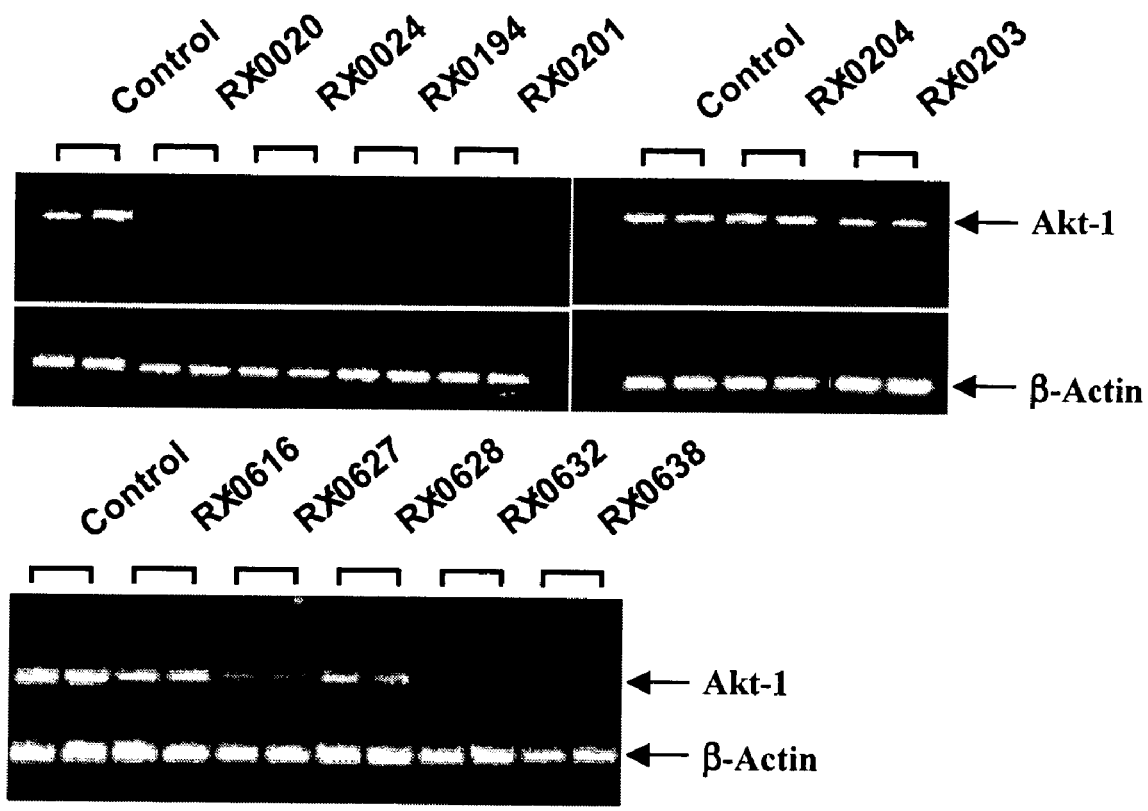
Fig. 1. RT-PCR analysis of Akt-1 inhibition by various oligonucleotides

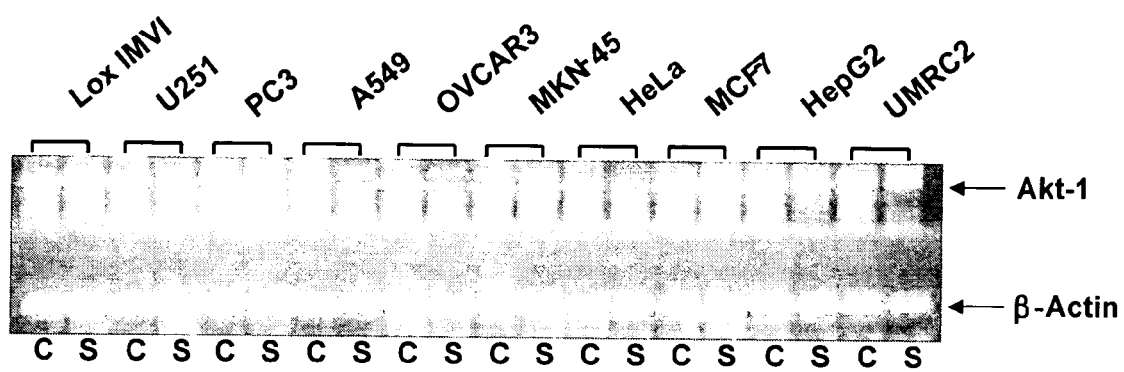
Fig. 2. RX-0194 inhibits Akt-1 mRNA expression in various cancer cell lines (C: control, S: RX-0194)

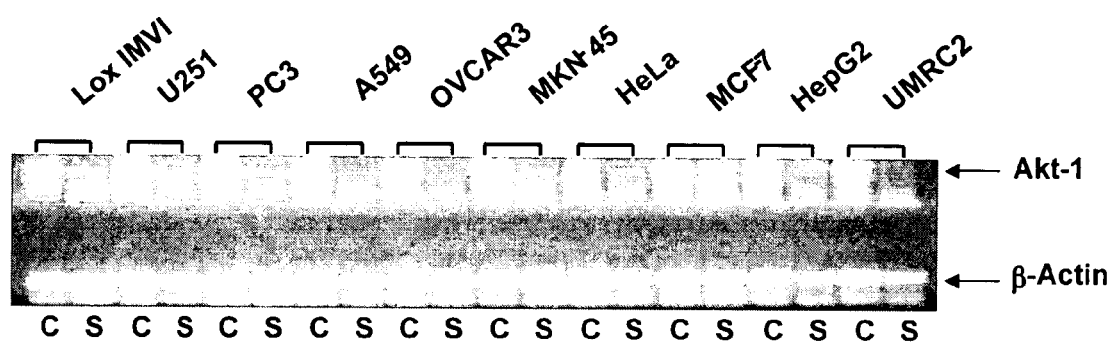
Fig. 3. RX-0201 inhibits Akt-1 mRNA expression in various cancer cells (C: control, S: RX-0201)

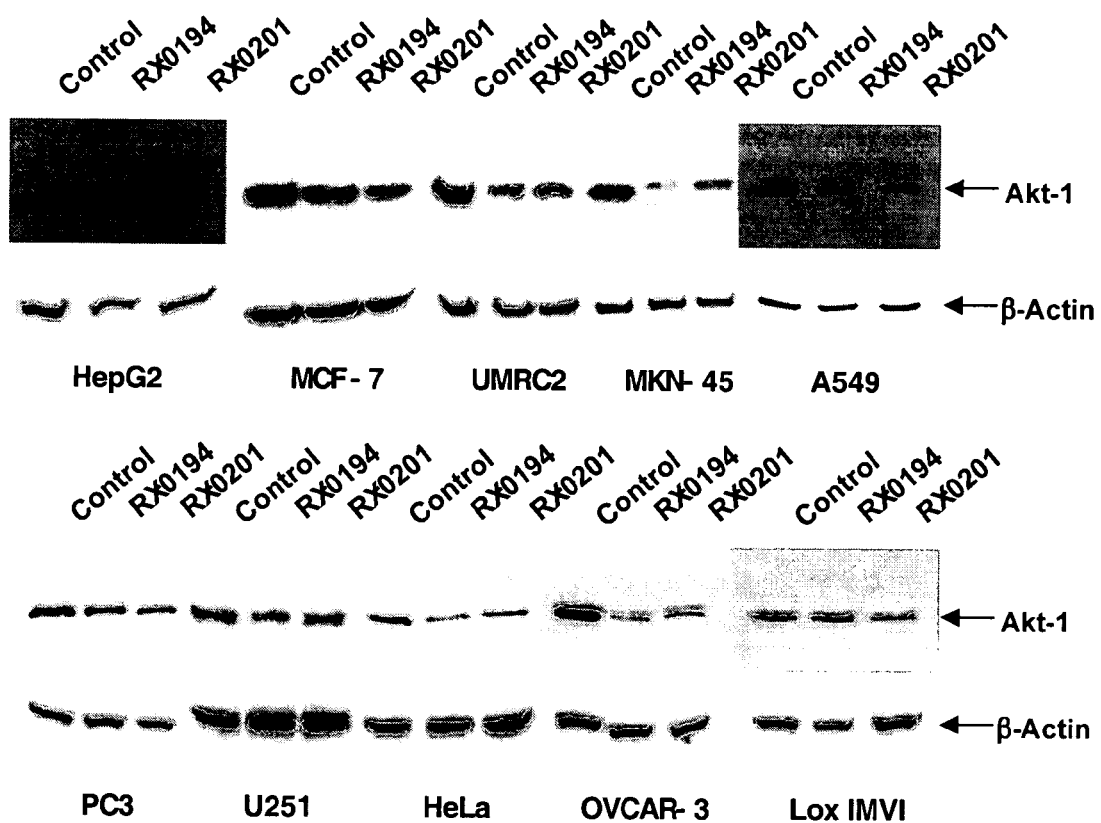
Fig. 4. Western blot analysis of inhibition of Akt-1 protein expression by RX-0194 and RX-0201

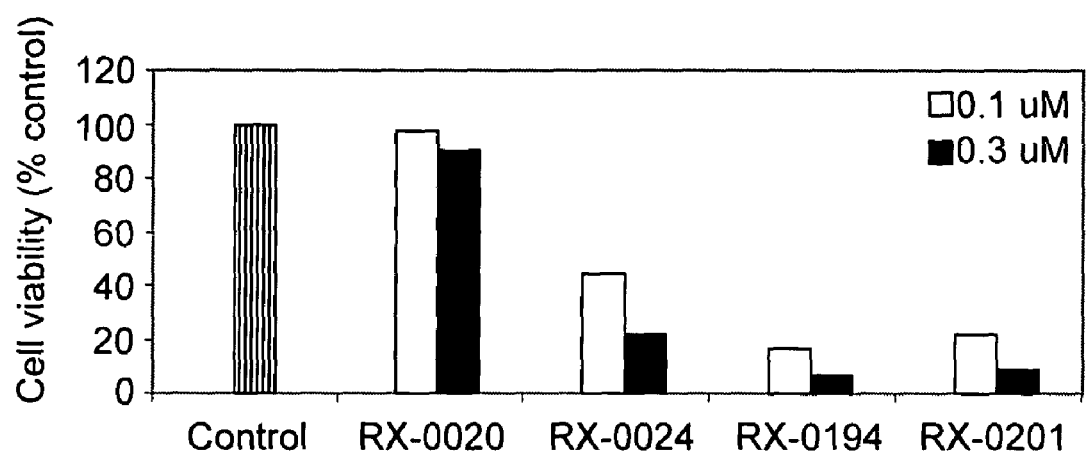
Fig. 5. Cytotoxicity test of various oligonucleotids in UMRC2 cells

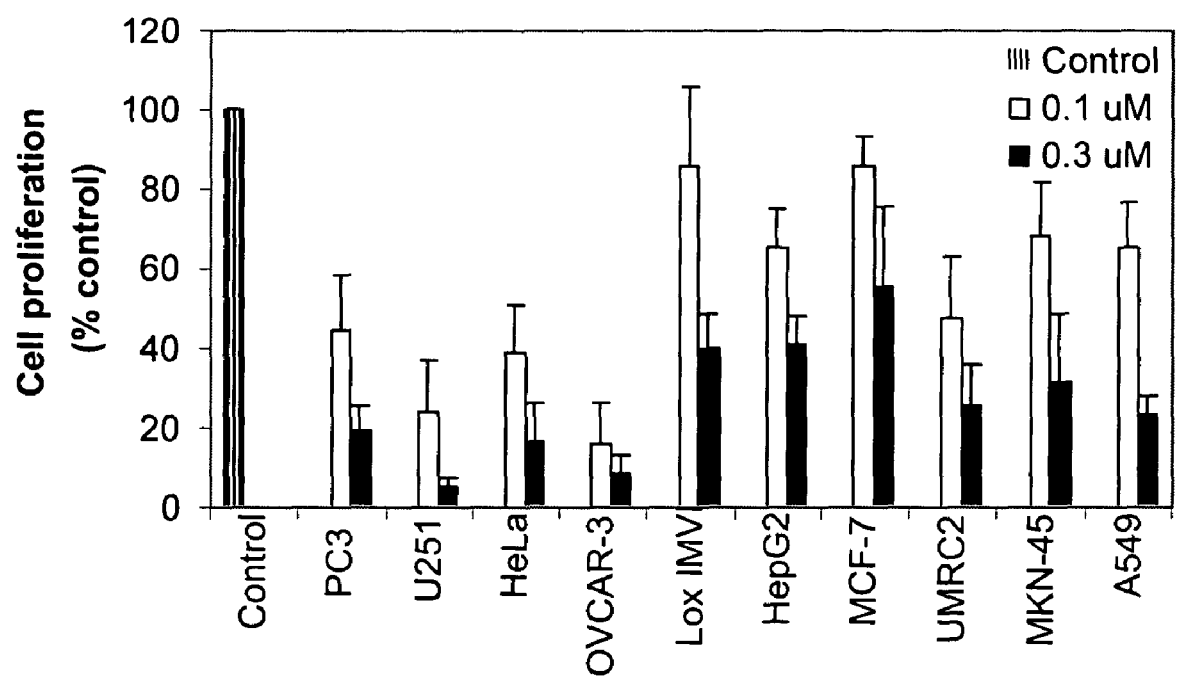
Fig. 6. RX-0194 causes cell cytotoxicity in various cancer cells

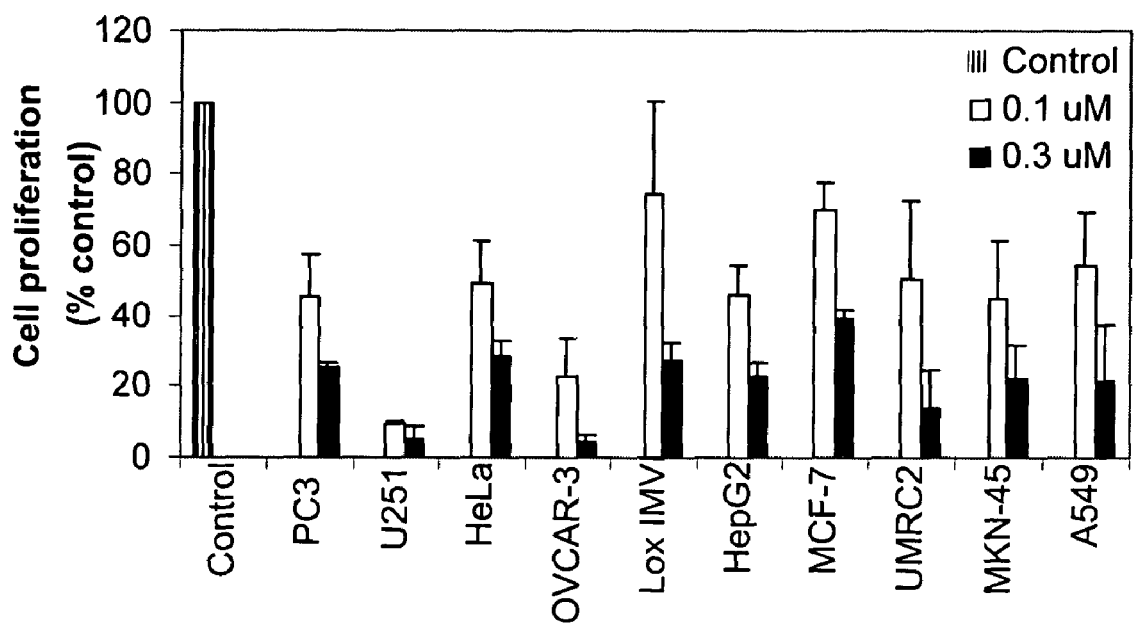
Fig. 7. RX-0201 causes cell cytotoxicity in various cancer cells

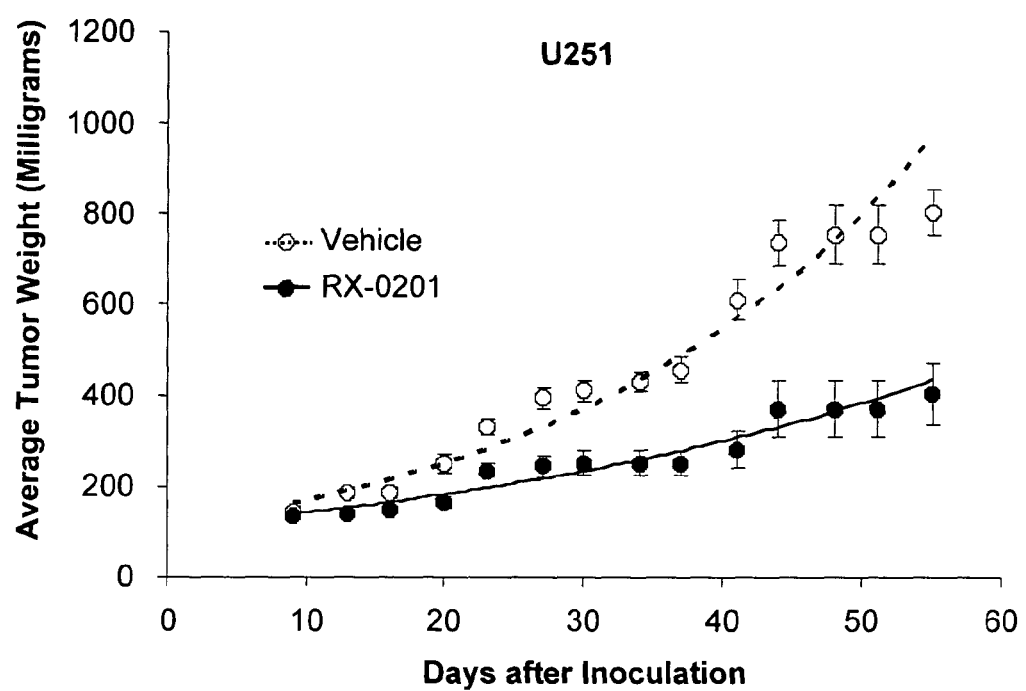
Fig. 8A. RX-0201 causes tumor weight loss in nude mice implanted with U251 human brain glioblastoma cells.

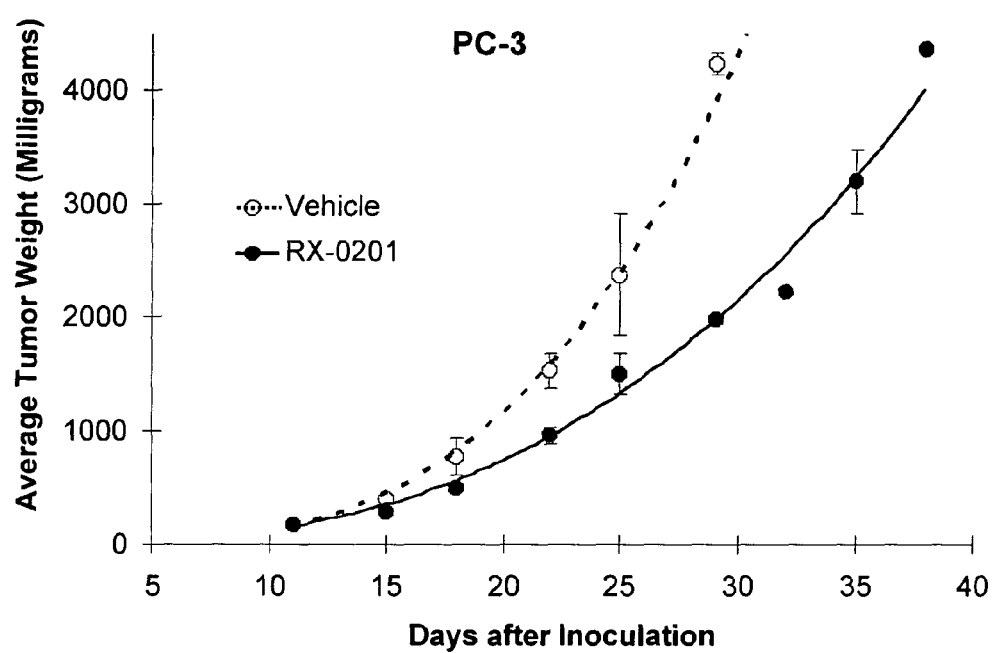
Fig. 8B. RX-0201 causes tumor weight loss in nude mice implanted with PC-3 human prostate adenocarcinoma cells.

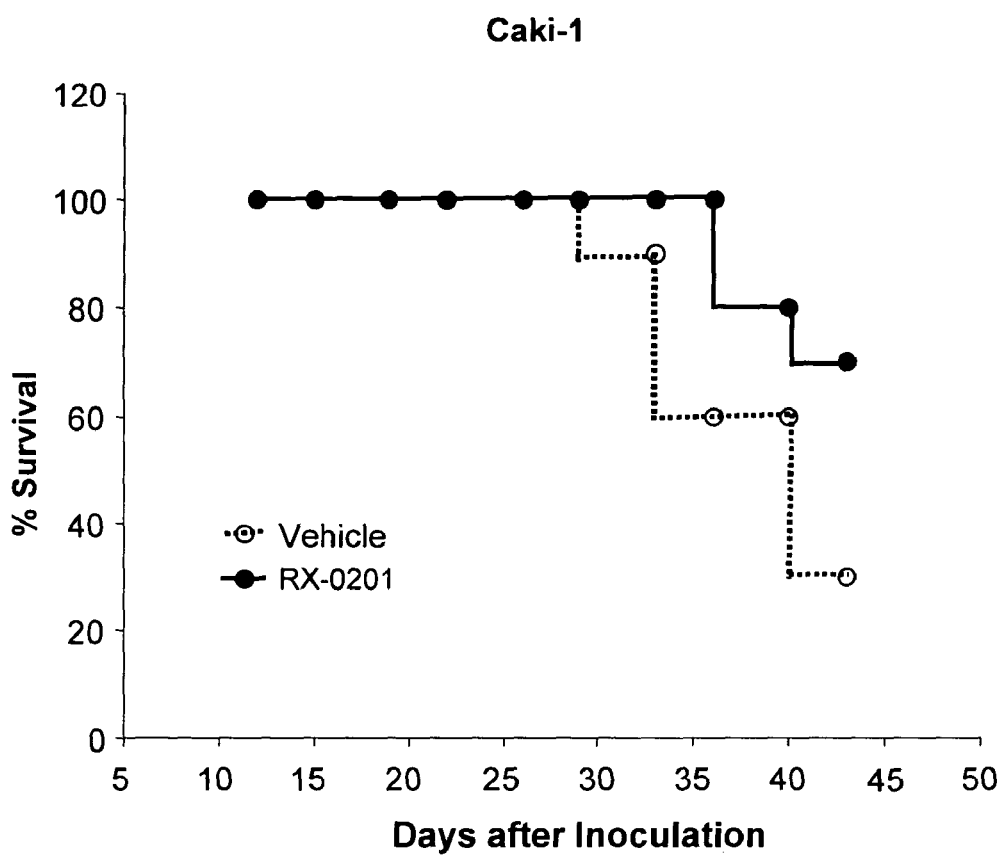
Fig. 9A. RX-0201 extends tumor survival rate in nude mice implanted with Caki-1 human renal carcinoma cells.

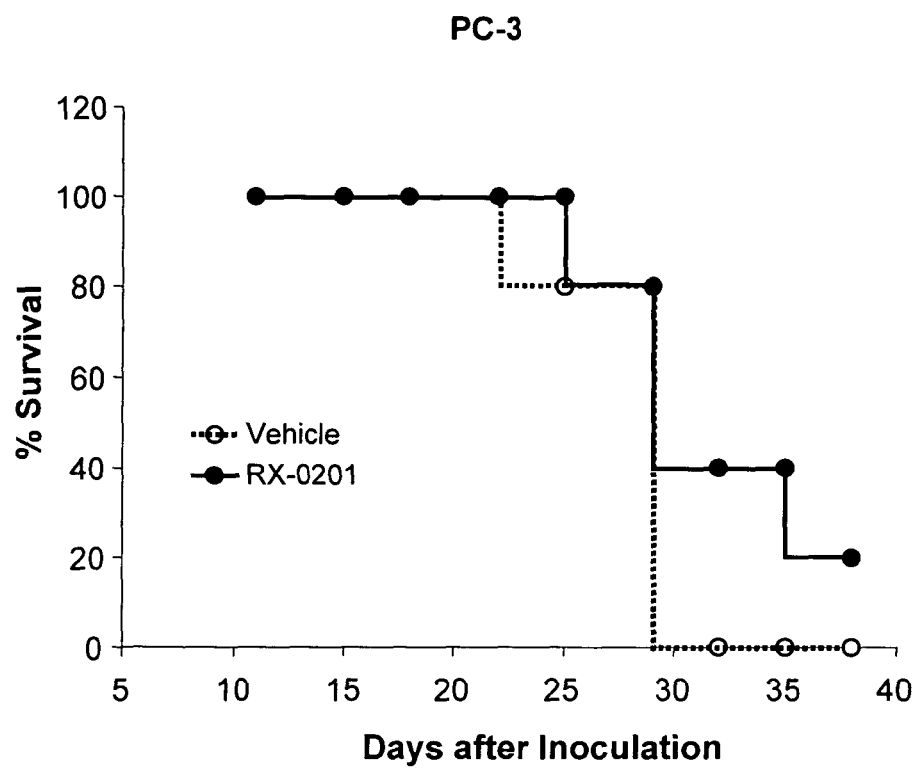
Fig. 9B. RX-0201 extends tumor survival rate in nude mice implanted with PC-3 human prostate adenocarcinoma cells.

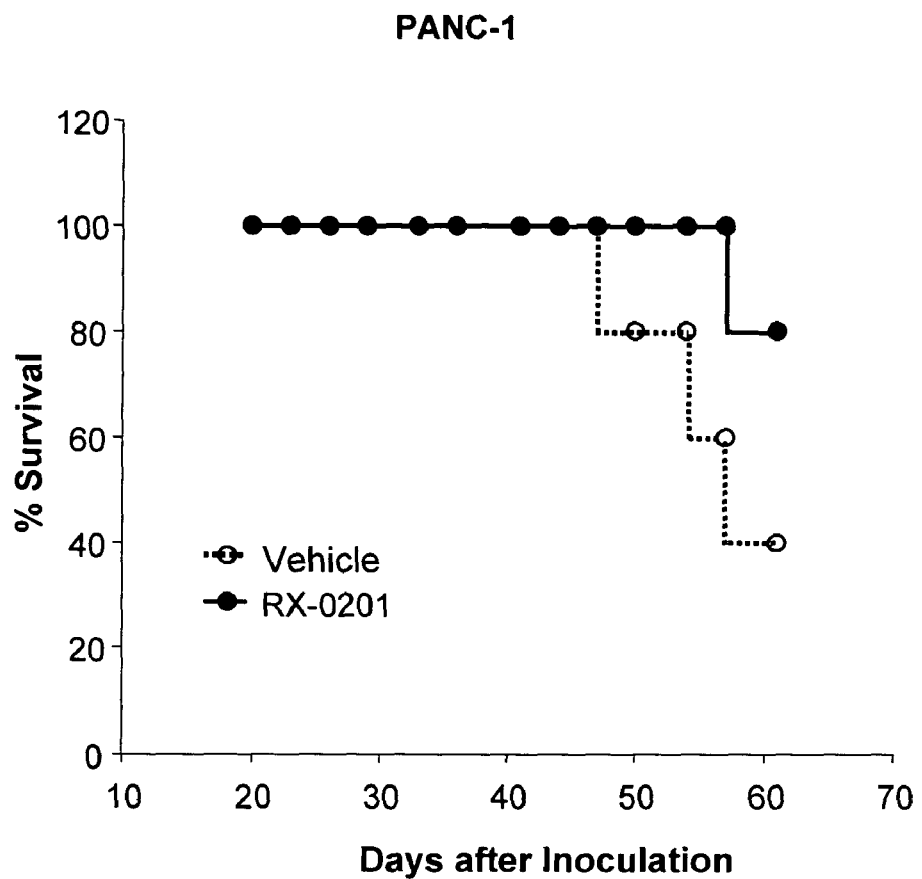
Fig. 9C. RX-0201 extends tumor survival rate in nude mice implanted with PANC-1 human pancreatic carcinoma cells.

USE OF ANTISENSE OLIGONUCLEOTIDES TO INHIBIT THE EXPRESSION OF HUMAN AKT-1

RELATED APPLICATION

This application is a continuation-in-part of U.S. Ser. No. 60/404,010 filed Aug. 16, 2002. A corresponding PCT Application, PCT/U.S. 03/25250 is filed concurrently herewith. Both applications are incorporated herein as if set forth in full.

SEQUENCE LISTING

This application incorporates by reference the material on the accompanying compact disc containing the file titled "7032 SEQUENCE LISTING.doc," sized 40 Kb created 13 Aug. 2003, which is an electronic copy of the file used to print the paper version of the sequence listing filed herewith.

FIELD OF THE INVENTION

This invention relates to new antisense oligonucleotide compounds, RX-0194, RX-0201, RX-0616, RX-0627, RX-0628, RX-0632 and RX-0638, that inhibit expression of a human protein, Akt-1, and also induce cytotoxicity in several cancer cell lines.

BACKGROUND OF THE INVENTION

The protein, Akt-1, is a signaling protein that is produced in increased amounts by several kinds of human cancer cells. This protein is believed, among other things, to be involved in a complex process that transmits a survival signal to cells under stress, which may allow preferential survival of tumor cells by helping them avoid the normal progression to apoptosis, or cellular death. This protein is also involved in the transmission of control signals related to important physiological functions, such as insulin metabolism and protein synthesis, as well as various aspects of cell growth and differentiation, including the growth of platelets, skin cells, and fibroblasts. Alteration of the Akt-1 protein can have a pleiotropic effect. That is, mutation of the protein can result in multiple, apparently unrelated, effects within an animal's cells. These effects point to the importance of Akt-1, and its potential usefulness in the treatment of disease, provided the appropriate precision in use can be obtained. Thus, the objective here is to inhibit the production of Akt-1 in the right context, that is, when it sends an undesirable survival signal to cancer cells.

Akt-1 exerts its effect through a process known generally as cell signaling. Cell signaling is a mechanism, or biological pathway, that regulates cell growth and survival. Various chemicals produced by the body, such as growth factors and cytokines, function as extracellular signals that interact with a cell's membrane. The membrane propagates the signals to the inside the cell, where various biological effects are manifested. A signal pathway is activated when an external signaling molecule, or ligand, binds to the cell membrane, and a protein kinase or a phosphatase modifies a target protein at a specific location on the molecule. Protein kinases are enzymes that (along with other materials such as phosphatases) regulate the propagation of the extracellular signals to inside of the cell. Protein kinases function to phosphorylate proteins at specific locations, namely at serine, threonine, and tyrosine residues. As a result, kinases are classified by their specific phosphorylation site. Akt-1 (also, "PKB alpha and RAC-PK alpha") is a member of the AKT/PKB family of serine/threonine kinases. In many signaling pathways, several steps using different kinases may be involved. An "upstream" kinase can phosphorylate, or activate, a "downstream target" protein, which may in turn be a kinase that has several targets. Cell signal propagation pathways are often found to be altered in cancer and other disease conditions. Such changes may indicate that this signaling pathway is affected when cells lose their normal signaling mechanism.

For example, tyrosine kinase activity, or signaling, becomes overactive in the early stages of cancer development, or oncogenesis. One consequence of this increased activity is an increased activity by another kinase, PI 3 kinase. PI 3 kinase is known to activate a number of members of the AKT/PKB family, and elevated levels of AKT/PKB have been observed in breast and other cancers. In a recent study, the function of Akt was the only factor found to be affected by an altered tumor suppressor gene, PTEN, in fruit flies. (Stocker, et al., *Science*, 2002, 295: 2088).

Due to its pleiotropic effect on, that is, its importance to, many metabolic pathways in the cell, Akt-1 has been extensively studied as a drug target for cancer and diabetes. Inhibitors of upstream kinases for Akt-1 have been the major focus on developing drugs that might change Akt-1 function. However, this approach was not yet proved specific enough, because the inhibitors were toxic to cells generally.

Other strategies aimed at inhibiting Akt-1 function have involved the use of various inhibitors for the upstream kinases immediately responsible for phosphorylating Akt-1. However, these strategies are not specific to Akt-1, and other important proteins were altered as well.

Another approach has been proposed, namely to use antisense oligonucleotides, to modify small portions of the gene that controls the expression, or production of, Akt-1.

U.S. Pat. No. 5,958,773 issued to Monia, et al., Sep. 28, 1999, relates to the use of various antisense oligonucleotides for the modulation of expression of nucleic acids encoding Akt-1. Results are reported in terms of inhibition of production of Akt-1. The specific oligonucleotides disclosed and claimed in the present invention were not disclosed in that patent.

BRIEF DESCRIPTION OF THE DRAWINGS

FIG. 1. RT-PCR analysis of Akt-1 inhibition by various oligonucleotides

FIG. 2. RX-0194 inhibits Akt-1 mRNA expression in various cancer cells

FIG. 3. RX-0201 inhibits Akt-1 mRNA expression in various cancer cells

FIG. 4. Western blot analysis of inhibition of Akt-1 protein expression by RX-0194 and RX-0201

FIG. 5. Cytotoxicity test of various oligonucleotides in UMRC2 cells

FIG. 6. RX-0194 causes cell cytotoxicity in various cancer cells

FIG. 7. RX-0201 causes cell cytotoxicity in various cancer cells

FIG. 8A. RX-0201 causes tumor weight loss in nude mice implanted with U251 human brain glioblastoma cells.

FIG. 8B. RX-0201 causes tumor weight loss in nude mice implanted with PC-3 human prostate adenocarcinoma cells.

FIG. 9A. RX-0201 extends tumor survival rate in nude mice implanted with Caki-1 human renal carcinoma cells.

FIG. 9B. RX-0201 extends tumor survival rate in nude mice implanted with PC-3 human prostate adenocarcinoma cells.

FIG. 9C. RX-0201 extends tumor survival rate in nude mice implanted with PANC-1 human pancreatic carcinoma cells.

SUMMARY OF THE INVENTION

The present invention is directed to antisense oligonucleotides, which are targeted to a nucleic acid encoding Akt-1, and which modulate the expression of Akt-1. Also provided is a method of inhibiting expression of Akt-1 in cells comprising contacting the cells with the oligonucleotide compounds and compositions of the invention. An advantage of the presently described oligonucleotides is that, in addition to inhibiting expression of Akt-1, they have a cytotoxic effect on several different cancer cell lines. The advantages of the present invention can be obtained by contacting cells of various cancer cell lines with an antisense compound that is specifically hybridizable to a site on the Akt-1 gene having the following sequence: 5' agtggactggtggggctgg 3' at site 1,271 of Akt-1 gene (Genebank # BC000479) (Seq. Id. No. 1). Particularly preferred is RX-0194, comprising 5' ccagcccccaccagtccact 3' (Seq. Id. No. 2). Similar advantages can be obtained with a compound that is antisense to the sequence 5' cgccaaggagatcatgcagc 3' at site 1,478 of Akt-1 gene (Genebank # BC000479) (Seq. Id. No. 3). Particularly preferred is RX-0201, comprising, 5' gctgcatgatctccttggcg 3' (Seq. Id. No. 4). The contact occurs under conditions that allow the oligonucleotide to hybridize with the gene encoding Akt-1. After hybridization, the ability of the cells to produce Akt-1 is inhibited, and cancer cell viability is reduced. In addition to the above 2 oligonucleotides, 5 additional antisense oligonucleotide compounds which also down-regulated Akt-1 mRNA expression and caused cytotoxic effects on cancer cell lines are described in the present invention. The 5 additional sequences are RX-0616, comprising 5' agatagctggtgacagacag 3' (Seq. Id. No. 13) hybridizable to the site beginning at position 2101 of Akt-1 gene, having the following sequence: 5' ctgtctgtcaccagctatct 3' (Seq. Id. No. 18, Genebank # BC000479);

RX-0627, comprising 5' cgtggagagatcatctgagg 3' (Seq. Id. No. 14) hybridizable to the site beginning at position 2473 of Akt-1 gene, having the following sequence: 5' cctcagatgatctctccacg 3' (Seq. Id. No. 19, Genebank # BC000479);

RX-0628, comprising 5' tcgaaaaggtcaagtgctac 3' (Seq. Id. No. 15) hybridizable to the site beginning at position 2493 of Akt-1 gene, having the following sequence: 5' gtagcacttgaccttttcga 3' (Seq. Id. No. 20, Genebank # BC000479);

RX-0632, comprising 5' tggtgcagcggcagcggcag 3' (Seq. Id. No. 16) hybridizable to the site beginning at position 2603 of Akt-1 gene, having the following sequence: 5' ctgccgctgccgctgcacca 3' (Seq. Id. No. 21, Genebank # BC000479); and RX-0638, comprising 5' ggcgcgagcgcgggcctagc 3' (Seq. Id. No. 17) hybridizable to the site beginning at position 170 of Akt-1 gene, having the following sequence: 5' gctaggcccgcgctcgcgcc 3' (Seq. Id. No. 22, Genebank # BC000479).

DETAILED DESCRIPTION OF THE INVENTION

The recent characterization of the AKT (sometimes referred to as PKB) family of serine/threonine kinases, the materials that promote or inhibit its production by cells, that is, its "upstream regulators", and the materials it acts upon, that is its "substrates" or "downstream targets", uncovered essential roles for this family in cell growth, survival and metabolism. PKB (protein kinase B) was originally found as a retroviral oncogene. Currently, three variants of the AKT family, Akt-1, Akt-2 and Akt-3 have been characterized. In a number of cancers, Akt genes are amplified, or the protein is overexpressed, indicating the important role it plays when cells become malignant. AKT/PKB is a growth-factor regulated serine/threonine kinase which contains a PH (pleckstrin homology) domain. This PH domain interacts with lipid products of PI 3K (phosphatidylinositol 3-kinase), phosphatidylinositol-3,4-biphosphate and phosphatidylinositol-3,4,5-triphosphate which initiates translocation of Akt-1 from a cell's cytosol to its plasma membrane. This translocation is required in order to present AKT/PKB to an upstream activation kinase, PDK1 (phosphoinositide-dependent kinase 1). A variety of growth factors such as PDGF, EGF, insulin, thrombin, and NGF are known to activate the translocation of AKT/PKB. It has been shown that Akt-1 induces cell survival and suppresses the apoptotic death of a number of cell types induced by a variety of stimuli, including growth factor withdrawal, cell cycle disruption, and loss of cell adhesion. The activated form of AKT/PKB protein phosphorylates numerous substrates, including GSK-3 (glycogen synthase kinase 3), eNOS (endothelial nitric oxide synthase), FKHR 1 (forkhead transcription factor family member 1), Bad (Bcl-2 pro-apoptotic family member), and p21 CIP (inhibitor of cell cycle progression). These actions can result in a various diverse biological effects such as suppression of apoptosis, control of glucose metabolism, cell proliferation, transcription, translation, cell migration and angiogenesis. Akt-1 has an anti-apoptotic activity which correlates with its activation when cells become cancerous. It is believed that the phosphorylation of Akt-1 triggers nucleo-cytoplasmic localization of substrates involved in cell cycle and apoptosis. This leads to a host of events culminating in malignancy, including acquired growth signal autonomy, insensitivity to apoptotic signals, unlimited replication, sustained angiogenesis, tissue invasion, and metastasis.

Given the pivotal role of the AKT/PKB family of serine/threonine kinases in the development of cancers, it would be desirable to inhibit its operation during oncogenesis. However, it would also be desirable, to the extent possible, to avoid interrupting the family's roles in other aspects of cellular metabolism. One approach might be to identify the gene that encodes a likely oncogenic kinase, and devise an antisense oligonucleotide that can be used to inhibit that gene's activity in the right context. U.S. Pat. No. 5,958,773 reported a wide variety of antisense oligonucleotides that can be used to inhibit production of Akt-1 in cancer cells. The inventors have found that several antisense oligonucleotides both exhibit an enhanced ability to inhibit the production of protein by the Akt-1 gene, and further, induce cytotoxicity in a variety of cancer cell lines.

An antisense compound is a tool that can be used to introduce modifications into the nucleic acids found in living cells. The term "antisense" refers to the notion that nucleic acids "encode" proteins. That is, the sequence of nucleotides found in a given nucleic acid determines, among other things, what protein will be produced. A "sense" sequence for a full gene will yield a normal protein in the usual amount, in response to a given stimulus. A "sense" oligonucleotide will hybridize with a normal gene sequence, and will not affect the amount of, or properties of, the protein. A "nonsense" sequence will not yield a product, or may yield a non-functional product. For example, if a "nonsense" codon or oligomer is inserted into a gene, a truncated, non-functional protein may result. An "antisense" oligonucleotide will hybridize with a normal gene, but will yield a protein altered with respect to its structure, or amount. It has been found that antisense oligomers, that is antisense compounds that are relatively short, can be easily inserted into cells, where they alter gene function.

Antisense compounds are commonly used as research reagents for the exploration of gene function because they are able to alter gene expression with exquisite specificity, and may be used to elucidate the function of particular genes. Antisense compounds can be used, for example, to distinguish between functions of various members of a biological pathway.

Antisense oligonucleotides can be used to selectively block disease-causing genes, thereby inhibiting production of disease-associated proteins. Some antisense oligonucleotides have been safely and effectively administered to humans, and numerous clinical trials are presently underway. It is thus possible that oligonucleotides can be used to treat cells, tissues, and animals, especially humans. In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for a nucleic acid target and increased stability in the presence of nucleobases.

The present invention employs oligomeric nucleotide compounds, particularly antisense oligonucleotides, which are targeted to a portion of a nucleic acid encoding Akt-1, and which modulate the expression of Akt-1. The oligonucleotide compounds are designed to specifically hybridize with one or more nucleic acids encoding Akt-1. One oligonucleotide, RX-0194, is targeted to a site on the Akt-1 gene having the following sequence: 5' agtggactggtgggggctgg 3' at site 1,271 of Akt-1 gene (Genebank # BC000479) (Seq. Id. No. 1). The sequence for the backbone of RX-0194 is complementary to this site. The inventors have found that oligomers comprising either 5 or 10 nucleotide upstream and downstream from the sequence where the 20-mer of RX-0194 was derived showed a measurable inhibition of Akt-1 mRNA expression. The other oligonucleotide, RX-0201, is targeted to a site in the coding region of the Akt-1 gene having the following sequence: 5' cgccaaggagatcatgcagc 3' at site 1,478 of Akt-1 gene (Genebank # BC000479) (Seq. Id. No. 3). The sequence for the backbone of RX-0201 is complementary to this site. The inventors have found that, this oligonucleotide is more sensitive to variability, and that while 18-mer of RX-0201 showed some inhibition of Akt-1 mRNA expression, further truncation from either end resulted in a substantial loss of inhibition of Akt-1 mRNA expression. The oligomers comprising either 5 or 10 nucleotide upstream and downstream from the sequence where the 20-mer of RX-0194 was derived demonstrated an inhibition of proliferation of cancer cells. The truncated versions of RX-0194 and RX-0201 also showed an inhibition of cancer cell proliferation. In addition to the above 2 oligonucleotides, 5 additional antisense oligonucleotide compounds which also down-regulated Akt-1 mRNA expression and caused cytotoxic effects on cancer cell lines are described in the present invention. The 5 additional sequences are RX-0616, comprising 5' agatagctggtgacagacag 3' (Seq. Id. No. 13) hybridizable to the site beginning at position 2101 of Akt-1 gene, having the following sequence: 5' ctgtctgtcaccagctatct 3' (Seq. Id. No. 18, Genebank # BC000479);

RX-0627, comprising 5' cgtggagagatcatctgagg 3' (Seq. Id. No. 14) hybridizable to the site beginning at position 2473 of Akt-1 gene, having the following sequence: 5' cctcagatgatctctccacg 3' (Seq. Id. No. 19, Genebank # BC000479);

RX-0628, comprising 5' tcgaaaaggtcaagtgctac 3' (Seq. Id. No. 15) hybridizable to the site beginning at position 2493 of Akt-1 gene, having the following sequence: 5' gtagcactgacctttcga 3' (Seq. Id. No. 20, Genebank # BC000479);

RX-0632, comprising 5' tggtgcagcggcagcggcag 3' (Seq. Id. No. 16) hybridizable to the site beginning at position 2603 of Akt-1 gene, having the following sequence: 5' ctgccgctgccgctgcacca 3' (Seq. Id. No. 21, Genebank # BC000479); and RX-0638, comprising 5' ggcgcgagcgcgggcctagc 3' (Seq. Id. No. 17) hybridizable to the site beginning at position site 170 of Akt-1 gene, having the following sequence: 5' gctaggcccgcgctcgcgcc 3' (Seq. Id. No. 22, Genebank # BC000479).

To target an antisense compound to a particular gene means to identify the nucleic acid sequence of interest, and select one or more sites within the nucleic acid sequence to be modified. Once the target site has been identified, an oligonucleotide is chosen which is sufficiently complementary to the target site so that it will hybridize specifically to the site, i.e., hybridize sufficiently well and with sufficient specificity, to give the desired effect.

As used herein, the phrase "nucleic acid encoding Akt-1" encompasses DNA encoding Akt-1, RNA (including pre-mRNA) transcribed from such DNA, and also cDNA derived from such RNA. The specific hybridization of an antisense oligomeric compound with its target nucleic acid interferes with the normal function of the nucleic acid. The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression, or production of, a protein. In the context of the present invention, "modulation" means either an increase (stimulation) or a decrease (inhibition) in the expression of a gene. For the present purposes, the gene encoding Akt-1 is modulated so that expression of Akt-1 is inhibited.

In the context of this invention, "to hybridize" means to hydrogen bond, which may be via Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 10 to about 30 nucleobases. Particularly preferred are antisense oligonucleotides comprising about 20 nucleobases (i.e. about 20 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'–5' linkages, 2'–5' linked analogs of these, and those having inverted polarity wherein the adjacent pairs of nucleoside units are linked 3'–5' to 5'–3' or 2'–5' to 5'–2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—]. Also preferred are oligonucleotides having morpholino backbone structures.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$$OCH_3$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486–504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, as described in examples hereinbelow.

Other preferred modifications include 2'-methoxy (2'-O—CH$_3$), 2'-aminopropoxy (2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-Me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. and are presently preferred base substitutions, even more particularly when combined with 2'-O-methoxyethyl sugar modifications.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethyl-ammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding Akt-1, enabling sandwich and other assays to easily be constructed to exploit this fact. Hybridization of the antisense oligonucleotides of the invention with a nucleic acid encoding Akt-1 can be detected by means known in the art. Such means may include conjugation of an enzyme to the oligonucleotide, radiolabelling of the oligonucleotide or any other suitable detection means. Kits using such detection means for detecting the level of Akt-1 in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

EXAMPLES

The following examples illustrate the practice of various aspects of the present inventions. They do not limit the inventions, or the claims, which follow them.

Example 1

Growth of Cancer Cell Lines

Cancer cells used to determine the effect of oligonucleotide compounds were obtained from the following sources: Human OVCAR-3 (ovary), MCF-7 (breast, hormone-dependent), HeLa (cervix), PC3 (prostate), HepG2 (liver), A549 (lung), Caki-1 (kidney), HT-29 (colon) and PANC-1 (pancreas) from the American Type Culture Collection (ATCC) (Manassas, Va.); U251 (brain) from Riken (Japan); MKN-45 (stomach) from DSMZ (Germany); UMRC2 (kidney) and Lox IMVI (melanoma) from the United States National Cancer Institute (Bethesda, Md.). All cell lines except UMRC2, Caki-1 and PANC-1 were grown in RPMI1640 medium (Invitrogen, Carlsbad, Calif.) supplemented with 10% fetal bovine serum ("FBS"), 1 mM sodium pyruvate, 10 mM HEPES and 100 U/ml penicillin and 100 μg/ml streptomycin ("P/S"). UMRC2, Caki-1 and PANC-1 cells were maintained in Dulbecco's modified Eagle's medium ("DMEM", Invitrogen) supplemented with 10% FBS, P/S, 10 mM HEPES and 2 mM L-glutamine. All cells were incubated at 37° C. under humidified 5% $CO_2$.

Example 2

Synthesis of Oligonucleotides

Various nucleotide sequences found in the human Akt-1 gene coding region known as the open reading frame ("ORF") and 3' untranslated region ("3' UTR") were selected as targets, and the corresponding complementary oligonucleotides synthesized. The backbone of each oligonucleotide was modified during synthesis to introduce phosphorothioate linkages between nucleotides, except at the 3' and 5' ends, so that an antisense oligonucleotide resulted.

Oligonucleotides located in the coding region of Akt-1 were synthesized using 8909 Expedite DNA synthesizer from Applied Biosystems, Foster City, Calif. ("ABI"). The synthesis of phosphorothioates was conducted the same manner as for the corresponding phosphodiester oligonucleotides except the standard oxidation bottle was replaced by 0.2 M 3H-1,2-benzodithiole-3-one 1,1-dioxide in acetonitrile for the stepwise thiation of the phosphite linkages. After cleavage from the controlled pore glass column and deblocking in concentrated ammonium hydroxide, the oligonucleotide compound was heated in the presence of ammonium hydroxide at 55° C. overnight. The supernatant was transferred to a new tube and ammonium hydroxide was evaporated by Speedvac plus and UVS400 Universal Vacuum System (Thermo Savant, Holbrook, N.Y.). The oligonucleotide was precipitated with 75 mM NaOAc, pH 7.2 and 2.5 volumes of ethyl alcohol and washed once with ethyl alcohol. The oligonucleotide was dissolved in water and the oligonucleotide concentration was measured by UV spectrophotometer.

Example 3

Transfection

Lipofectamine PLUS reagent was used in transfection procedures for RNA and protein analysis. The day before transfection, cells were trypsinized, counted and plated. For 6 well-plate each well $2.5 \times 10^5$ cells of UMRC2 were plated so that they reach 50–90% confluency at the day of transfection. All the reagents and media used for transfection experiment were obtained from Invitrogen (Carlsbad, Calif.). The following solutions were prepared in sterile tubes: Solution A: for each transfection, a mixture of 2 μl (0.5 μg) DNA, 100 μl of serum free medium ("Opti-MEM") and 3 μl PLUS reagent was incubated at room temperature for 15 minutes. Solution B: for each transfection, a mixture of 2.5 μl of Lipofectamine Reagent and 100 μl of serum free medium (Opti-MEM). Solutions A and B were combined and incubated at room temperature for 15 minutes. For transfection, cells were washed once with 2 ml of serum free medium (Opti-MEM) or PBS and 800 μl of serum free medium (Opti-MEM) were added to each well. The combined solution A and B was added to each well and mixed gently. Subsequently cells were incubated for 3 to 4 hours at 37° C., the medium was replaced with regular medium and incubated for the indicated time. Two different transfection reagents were used to perform $IC_{50}$ measurements of cell growth inhibition. In addition to the Lipofectamine PLUS reagent described above, Lipofectamine 2000 was also used. The procedure using Lipofectamine 2000 was the same as described above, except that the wash step using PBS or serum free medium was omitted. The $IC_{50}$ values using Lipofectamine PLUS and Lipofectamine 2000 are shown in the Tables 2 and 3, respectively.

Example 4

Inhibition of Akt-1 mRNA Expression by Antisense Oligonucleotides

The antisense oligonucleotides were then tested for their ability to down-regulate, or inhibit, the expression of mRNA encoding Akt-1. The level of expression of Akt-1 mRNA in cells transfected with the antisense oligonucleotides was measured by RT-PCR analysis. Samples were taken at 6 hours after transfection, RNA was isolated and subjected to RT-PCR analysis.

UMRC2 cells ($2.5 \times 10^5$ cells per well) on a 6-well plate were transfected with the experimental oligonucleotides and the transfected cells were used to isolate total RNA. Total RNA was isolated by using RNA-STAT kit (TEL-TEST, Inc., Friendswood, Tex.), according to the supplier's manual [See also Chomczynski, P. and Sacchi, N in *Anal. Biochem.* 162: 156–159 (1987)]. Briefly, media were removed from the two 6-well plates and total 0.5 ml RNA-STAT solution was added and mixed by pipetting several times, and transferred to an eppendorf tube. 0.1 ml of chloroform was added to the tube, and the tube was shaken vigorously for 15 seconds, and then incubated for 3 minutes at room temperature before centrifugation at 14,000 rpm for 15 minutes at 4° C. The top layer was transferred to a new tube and 0.3 ml of isopropanol was added and incubated for 10 minutes at room temperature. Subsequently the RNA precipitate was centrifuged at 14,000 rpm for 10 minutes. The resulting pellet was washed with 70% ethanol, dried briefly and reconstituted with 20 μl water. RNA concentration was determined by spectrophotometer. RT reaction was carried out using M-MLV enzyme kit (Invitrogen). 5 μg of total RNA was used to synthesize cDNA in 20 μl RT reaction. First-strand cDNA was synthesized by incubating total RNA, oligo dT (0.5 mg) and dNTP (0.5 mM) mixture at 65° C. for 5 minutes and by quick-chilling on ice. First-strand buffer, 7.4 mM DTT and 1 μM-MLV Reverse Transcriptase (200 units) was added to the above reaction mixture and incubated at 37° C. for 50 minutes and the enzyme inactivation was followed at 70° C. for 15 minutes. Akt-1 cDNA synthesized by RT reaction was measured by PCR using Sapphire RCR mix (SuperBio Inc., Seoul, Korea) with appropriate primers. For Akt-1 mRNA detection, primers, 5' CTGGACAAG-GACGGGCACA 3' (Seq. Id No. 5) and 5' GGTGGGCT-GAGCTTCTTCTCGTA 3' (Seq. Id No. 6). Beta-actin was used as an internal PCR control. Primers for beta-actin were 5' CCCATGCCATCCTGCGTCTG 3' (Seq. Id. No. 7) and 5' ACGGAGTACTTGCGCTCAG 3' (Seq. Id. NO. 8). PCR products were analyzed on 1.5% agarose gel by electrophoresis.

A total of 86 oligonucleotides were initially screened and the results from eleven are shown in Table 1, below, and also in FIG. 1. Each oligonucleotide was retested to confirm the down-regulation of mRNA expression level. Each reaction was performed in duplicate.

TABLE 1

Expression of Akt-1 mRNA Inhibited

| Rexahn# | Region | Target Site* | 5'-Sequence-3' | Seq. Id. No. | % Inhibition |
|---|---|---|---|---|---|
| RX-0020 | Coding | 695 | ggtgcttgggcttggccagg | 9 | 92 |
| RX-0024 | 3'UTR | 1961 | ctgagggctgaggccacacc | 10 | 81 |
| RX-0194 | Coding | 1271 | ccagcccccaccagtccact | 2 | 82 |
| RX-0201 | Coding | 1478 | gctgcatgatctccttggcg | 4 | 90 |
| RX-0203 | Coding | 1202 | gtgccgcaaaaggtcttc | 11 | 40 |
| RX-0204 | 3'UTR | 1757 | gcctctccatccctccaa | 12 | 16 |
| RX-0616 | 3'UTR | 2101 | agatagctggtgacagacag | 13 | 20 |

TABLE 1-continued

Expression of Akt-1 mRNA Inhibited

| Rexahn# | Target Region | Site* | 5'-Sequence-3' | Seq. Id. No. | % Inhibition |
|---|---|---|---|---|---|
| RX-0627 | 3'UTR | 2473 | cgtggagagatcatctgagg | 14 | 50 |
| RX-0628 | 3'UTR | 2493 | tcgaaaaggtcaagtgctac | 15 | 40 |
| RX-0632 | 3'UTR | 2603 | tggtgcagcggcagcggcag | 16 | 76 |
| RX-0638 | 5'UTR | 170 | ggcgcgagcgcgggcctagc | 17 | 85 |

*Genebank #BC000479

RX-0203 and RX-0204 are sequences disclosed in U.S. Pat. No. 5,958,773, as Target Site Nos. 1116 and 1671 respectively (Genebank # M613167). These were chosen as representatives from two regions found in the reference, the ORF and 3' UTR regions of the Akt-1 gene, both exhibiting the highest % inhibition for that region according to the test used in that reference. All of the other oligonucleotides have new sequences designed by the inventors. All of the new sequences exhibited enhanced or comparable % inhibition over the reference, using the test described herein. However, it was found that % inhibition did not correlate with cytotoxicity, as discussed below in Example 6. Subsequently, two oligonucleotides that exhibited both high % inhibition of Akt-1 mRNA expression in UMRC2 cells and cytotoxicity were selected for testing in other cancer cell lines. An additional 5 sequences were also tested for cytotoxicity in cancer cell lines.

FIG. 2 shows down-regulation of Akt-1 mRNA level in ten cancer cell lines (UMRC2, OVCAR-3, MKN-45, A549, PC3, U251, Lox IMVI, HeLa, HepG2 and MCF-7) after transfection with 0.1 µM RX-0194. High level down-regulation of Akt-1 was observed in Lox IMVI, U251, PC-3, OVCAR-3, MKN-45, HeLa and A549 cell lines, moderate level down-regulation was found in MCF-7 and UMRC2 and low level down-regulation was observed in HepG2.

FIG. 3 shows down-regulation of Akt-1 mRNA level in ten cancer cell lines (UMRC2, OVCAR-3, MKN-45, A549, PC3, U251, Lox IMVI, HeLa, HepG2 and MCF-7) after transfection with 0.3 µM RX-0201. Marked to moderate down-regulation of Akt-1 was observed in all cell lines except in MCF-7 cells, which showed a low level of down-regulation.

Example 5

Western Blot Analysis of Akt-1 Protein Levels

Various cancer cell lines were transfected as described above in Example 3 with the preferred RX-0194 and RX-0201 oligonucleotides at a concentration of either 0.1 or 0.3 µM. About 24 hours after transfection, cells were washed once with PBS and resuspended with the lysis buffer containing 25 mM Tris-HCl, pH 7.5, 300 mM NaCl, 1% Triton X-100 and protease inhibitors (Roche Diagnostics Corp., Indianapolis, Ind.). Cells were sonicated by 10 second pulse three times using a Branson sonifier 450 and after 15 minute centrifugation at 14,000 rpm, the supernatant was transferred to a new tube. BCA protein assay reagent (Pierce Biotechnology, Rockford, Ill.) was used to measure protein concentration. Crude cell extracts were used to determine Akt-1 protein expression by SDS-PAGE and subsequent Western analysis using an anti-Akt1 antibody (Santa Cruz Biotechnology, Santa Cruz, Calif.). Anti-beta-actin antibody (Santa Cruz Biotechnology) was used as an internal control. Results are shown in FIG. 4. Both RX-0194 and RX-0201 demonstrated inhibition of Akt-1 protein expression, to a greater or lesser degree in all cell lines.

Example 6

Cell Cytotoxicity Test

Human cancer cell lines were used to test cell cytotoxicity of experimental oligonucleotides. Sulforhodamine B ("SRB") method [Skehan et al., *J. National Cancer Institute*, 82: 1107–1112 (1990)] was used to assess the cell survival after RX-oligonucleotide transfection.

Cells were plated onto a 96-well plate and transfected with the oligonucleotides the next day. Following a 72-hour incubation period, the surviving cells were stained with sulforhodamine B and measured using a microplate reader. Briefly, 1,000–10,000 cells were plated onto each well in a 96-well plate and transfected with experimental oligomers using Lipofectamine PLUS reagent (Invitrogen). After 3 to 4 hour incubation, the transfection agent was removed and the fresh media was added to each well. After 72 hours incubation, media was removed. Cells were fixed with 10% trichloroacetic acid ("TCA"), incubated for 1 hour at 4° C., and washed 4 times with tap water. Subsequently cells were stained with 0.4% sulforhodamine B in 1% acetic acid for 30 minutes, washed 4 times with 1% acetic acid, and air-dried again. After 5 minutes agitation in 10 mM Tris solution, optical density of the samples was read at 530 nm using Benchmark Plus Microplate reader (Bio-Rad Laboratories, Hercules, Calif.).

The experimental compounds which showed down-regulation of Akt-1 mRNA, were used to test their effect on UMRC2 cell viability. FIG. 5 shows results for RX-0020, RX-0024, RX-0194 and RX-0201. RX-0194 and RX-0201 showed the most potent cell cytotoxic effect compared with the other oligonucleotides tested. Interestingly, RX-0020 and RX-0024, new oligonucleotides that had exhibited 92 and 81% inhibition of mRNA respectively, did not exhibit as much cytotoxicity as RX-0194 and RX-0201.

The two best candidates, RX-0194 and RX-0201, were screened for cytotoxicity against a variety of cancer cell lines. As shown in FIG. 6, RX-0194 reduced cell viability in the following human cancer cell lines; PC3 (prostate), U251 (brain), HeLa (cervix), OVCAR-3 (ovary), Lox IMVI (melanoma), HepG2 (liver), MCF-7 (breast), UMRC2 (renal), MKN-45 (stomach) and A549 (lung). The cell cytotoxicity of RX-0194 increased with the concentration of RX-0194 among different cell lines tested. 0.1 µM of RX-0194 in PC3, U251, HeLa, OVCAR-3 and UMRC2 caused more than 50% of cell death. But more than 50% of cells in Lox IMVI, HepG2, MCF-7, MKN-45 and A549 survived at 0.1 µM. FIG. 7 shows that similar results were obtained for RX-0201. Again, cytotoxicity of RX-0201 was demonstrated in 10 cell lines, and it increased with concentration to varying degrees among the different cell lines. 0.1 µM of RX-0201 caused more than 50% cell death in PC3, U251, HeLa, OVCAR-3, HepG2, MKN-45 and UMRC2, but more than 50% of Lox IMVI, MCF-7 and A549 survived.

Example 7

$IC_{50}$ Measurement of Cell Cytotoxicity for RX-0194 and RX-0201 Oligonucleotides The experimental oligonucleotides were screened for relative effective dosage. Ten different cancer cell lines were transfected with RX-0194 or RX-0201 at concentrations ranging from 0.01 µM to 1 µM using Lipofectamine PLUS reagent and after 72 hours post-transfection, cells were stained with sulforhodamine B and the number of surviving cells were counted using Bio-Rad Microplate reader (Bio-Rad Laboratories). The $IC_{50}$ value, or concentration of drug needed to kill half the cells, was calculated using the KaleidaGraph Software (Synergy Software, Reading, Pa.) program. The results are reported in Table 2, below.

TABLE 2

| Cell RX- | PC3 | U251 | HeLa | OVCAR-3 | Lox-IMVI | HepG2 | MCF7 | UMRC2 | MKN-45 | A549 |
|---|---|---|---|---|---|---|---|---|---|---|
| | | | | | | $IC_{50}$ (µM) | | | | |
| 0194 | 0.098 | 0.046 | 0.08 | 0.034 | 0.31 | 0.2 | 0.47 | 0.1 | 0.17 | 0.13 |
| 0201 | 0.096 | 0.039 | 0.11 | 0.036 | 0.18 | 0.066 | 0.2 | 0.1 | 0.093 | 0.11 |

For comparison, it is noted that the $IC_{50}$ for UMRC2 is 0.1 µM for RX-0194 and 0.1 µM for RX-0201. When the compounds RX-0203 and RX-0204 were tested in the same manner, $IC_{50}$ values for UMRC2 were 0.35 µM and 0.44 µM respectively. That is, three to four times as much of RX-0203 and RX-0204 was needed to obtain the same results as the newer compounds. RX-0194, RX-0201, RX-0203 and RX-0204 along with the additional 5 oligonucleotides, RX-0616, RX-0627, RX-0628, RX-0632 and RX-0638 were used to transfect various cancer cells using Lipofectamine 2000 reagent at 0.1 to 0.001 µM. After 72 hours, cells were stained with sulforhodamine B and the number of surviving cells were counted using Bio-Rad Microplate reader (Bio-Rad Laboratories). The $IC_{50}$ value, or concentration of drug needed to kill half the cells, was calculated using the KaleidaGraph Software (Synergy Software, Reading, Pa.) program. The results are reported in Table 3, below.

TABLE 3

| Cell line | RX-0201 | RX-0616 | RX-0632 | RX-0627 | RX-0628 | RX-0638 |
|---|---|---|---|---|---|---|
| | | | $IC_{50}$ (µM) | | | |
| UMRC2 | 0.015 | 0.017 | 0.014 | 0.018 | 0.020 | 0.028 |
| Caki-1 | 0.0092 | 0.0080 | 0.0040 | 0.0042 | 0.0058 | 0.014 |
| A549 | 0.0067 | 0.0086 | 0.0036 | 0.0054 | 0.011 | 0.014 |
| HeLa | 0.012 | 0.012 | 0.014 | 0.0086 | 0.014 | 0.021 |
| PANC-1 | 0.028 | 0.044 | 0.034 | 0.040 | 0.041 | 0.049 |
| U251 | 0.0050 | 0.011 | 0.016 | 0.0056 | 0.0086 | 0.015 |
| PC3 | 0.018 | 0.036 | 0.041 | 0.017 | 0.056 | 0.037 |
| HT29 | 0.042 | 0.062 | 0.076 | 0.043 | 0.051 | 0.038 |
| MKN-45 | 0.0064 | 0.0059 | 0.013 | 0.0062 | 0.0071 | 0.011 |
| OVCAR-3 | 0.0033 | 0.0095 | 0.0051 | 0.0035 | 0.0038 | 0.0037 |
| HepG2 | 0.019 | 0.023 | 0.032 | 0.021 | 0.036 | 0.028 |
| MCF7 | 0.020 | 0.020 | 0.028 | 0.020 | 0.027 | 0.024 |
| Lox IMVI | 0.018 | | | | | |

Similar to the cytotoxicity results obtained with Lipofectamine PLUS reagent, $IC_{50}$ values for RX-0203 and RX-0204 were 3 to 6 times higher than those of RX-0201 when Lipofectamine 2000 reagent was used for transfection in several cancer cell lines. This indicates that RX-0201 was more efficient at inducing cytotoxicity than the prior art compounds. Furthermore, results comparable to those obtained with RX-0201 were obtained with RX-0616, RX-0632, RX-0627, RX-0628 and RX-0638. As shown in Table 3, $IC_{50}$ values were significantly lower when Lipofectamine 2000 reagent was used for the measurements.

Example 8

Sequence Variability

In order to determine whether the full 20-mer backbone of RX-0194 and RX-0201 are required to down-regulate Akt-1 mRNA expression, 18-, 16-, 14-, and 10-mer oligonucleotides were synthesized and their effects on mRNA expression and cytotoxicity were analyzed. RT-PCR analysis data indicated that the 18-, 16- and 14-mer versions of RX-0194 showed stronger inhibition of Akt-1 mRNA expression than the 20-mer version of RX-0194. This suggests that the sequence truncation of RX-0194 down to 14-mer did not adversely affect the desired inhibition of Akt-1 mRNA expression. However, the 10-mer of RX-0194 did not show much inhibition. For RX-0201, the 18-mer version of RX-0201 showed some inhibition of Akt-1 mRNA expression. However, when the sequence was truncated to the 16-, 14-, and 10-mer versions of RX-0201, the inhibition became insignificant. This indicates that for RX-0201, the 20-mer full-length sequence is required to achieve the maximum inhibition of Akt-1 mRNA expression.

In conjunction with the above data, we observed that oligomers comprising either 5 or 10 nucleotides, both upstream and downstream from the sequence where the 20-mer of RX-0194 was derived, showed a measurable inhibition of Akt-1 mRNA expression.

Cytotoxicity was tested using the same oligomers comprising 5 or 10 nucleotides upstream and downstream from the sequence where 20-mer of RX-0194 was derived in UMRC2, MKN-45, U251 and OVCAR-3 cell lines. All 4 modified oligomers demonstrated cytotoxic effects comparable to the 20-mer of RX-0194, consistent with the RT-PCR data. The truncated versions of RX-0194 and RX-0201 described above also showed a strong inhibition of cancer cell proliferation.

Example 9

Ex Vivo Xenograft Study

In order to observe the inhibition of growth of various tumors by one of the RX compounds, RX-0201, in animal models, an ex vivo xenograft study of nude mice was conducted. Thirty to forty mg fragments of a human tumor, such as U251, PC-3, Caki-1 and PANC-1 from an existing in vivo passage were implanted subcutaneously (sc) into mice near the right axillary area, using a 12-gauge trocar needle. The day of tumor implant was designated as day 0. Tumors were allowed to reach 75–250 mm$^3$ in size (an estimated 75-250 mg in weight) before the start of treatment with RX-0201. A sufficient number of mice were implanted with fragments so that tumors in a weight range as narrow as possible were selected for the trial on the day of treatment initiation. Those animals selected with tumors in the proper size range were assigned to various treatment groups. The time from the day when the tumor fragments were implanted to the day when the tumors were in the range of 75–250 mg is different for each tumor, thus, the first day of treatment will be different for each tumor model. The antisense oligonucleotide, RX-0201 in normal saline was administered by tail vein injection every other day for 3 weeks, unless otherwise noted, following the detection of a palpable tumor mass (50–100 mm$^3$). The oligonucleotides were administered at doses of 30 mg/kg or 60 mg/kg per injection. Control animals received normal saline alone, without oligonucleotide. Following treatment, the mice were observed for up to 30 more days to detect possible tumor regrowth.

The tumors were measured and the animals were weighed twice weekly starting with the first day of treatment. Tumor volume was determined by caliper measurements and using the formula for an ellipsoid sphere: $L \times W^2 / 2 = mm^3$, where L and W refer to the larger and smaller dimensions collected at each measurement. This formula was also used to calculate tumor weight, assuming unit density (1 mm$^3$=1 mg).

Suitable human cancer cell lines were those that have been tested already for inhibition of Akt-1, and those particularly preferred were brain glioblastoma U251, prostate adenocarcinoma PC-3, renal carcinoma Caki-1, and pancreatic carcinoma PANC-1. The antitumor efficacy of RX-0201 was evaluated against sc-implanted tumor xenografts in nude mice and tumor weights and survival rate were measured after the treatment of RX-0201. Tumor weights (mean±SEM) in each group of animals were presented in FIGS. 8A and 8B and the survival rate was measured in FIGS. 9A, 9B and 9C.

FIG. 8A shows the measurement of tumor weight as an indicator of efficacy of RX-0201 against athymic female Ncr-nu nude mice sc-implanted with U251 human glioblastoma xenografts. All treatments were initiated on day 9 postimplant, when the individual tumor sizes ranged from 75 to 221 mg. The RX-0201 treatment was well tolerated without deaths and no more than 1 g body weight fluctuations was observed. After day 27, the tumor weights were significantly reduced in the mice treated with RX-0201 at 30 mg/kg treatment compared to the controls.

FIG. 8B shows that the efficacy of RX-0201 treatment against male Ncr-nu mice sc-implanted with PC-3 human prostate tumor xenografts. All treatments were initiated on day 11 postimplant, when the individual tumor sizes ranged from 144 to 221 mg. After day 25, the tumor weights were reduced significantly in the mice treated with RX-0201 at 60 mg/kg level compared to the control animals.

To evaluate the survival rate of RX-0201 compound, sc-implanted, Caki-1 human renal tumor and PANC-1 human pancreatic tumor xenografted female NCr-nu mice were used in the tumor model study. As in the tumor weights measurement, male NCr-nu mice were used for the measurement of the survival rate in PC-3 tumor xenograft study. All treatments were initiated at day 11 and 12 postimplant for PC-3 and Caki-1, respectively and day 20 postimplant for PANC-1. As shown by Kaplan-Meyer plots, the percentage of live animals was plotted against day after inoculation. FIGS. 9A, 9B and 9C show that RX-0201 significantly increased the survival rate of the animals implanted with Caki-1 at 30 mg/kg dose level and PC-3 and PANC-1 at 60 mg/kg dose level.

What is claimed is:

1. A compound, RX-0194, having a sequence comprising Seq. Id. No. 2 5' ccagccccaccagtccact 3', targeted to a nucleic acid molecule encoding human Akt-1, wherein said oligonucleotide compound inhibits the expression of human Akt-1.

2. The compound of claim 1, wherein the compound is an antisense oligonucleotide.

3. The antisense oligonucleotide of claim 2 having at least one modified internucleoside linkage that is a phosphorothioate linkage.

4. A method of inhibiting the expression Akt-1 in human cells or tissues comprising contacting said cells or tissues with the compound of claim 1.

5. A method of inducing cytotoxicity in a cancer cell comprising the step of introducing into the cell an oligonucleotide that hybridizes to a human Akt-1 sequence, comprising, RX-0194, Seq. Id. No. 2, 5' ccagccccaccagtccact 3'.

6. A compound, RX-0201, 5' gctgcatuatctccttggcg 3', Seq. Id. No. 4, targeted to a nucleic acid molecule encoding Akt-1, wherein said compound inhibits the expression of human Akt-1.

7. The compound of claim 6, wherein the compound is an antisense oligonucleotide.

8. The antisense oligonucleotide of claim 7 having at least one modified internucleoside linkage that is a phosphorothioate linkage.

9. A method of inhibiting the expression of Akt-1 in human cells or tissues comprising contacting said cells or tissues with the compound of claim 6.

10. A method of inducing cytotoxicity in a cancer cell comprising the step of introducing into the cell an oligonucleotide that hybridizes to a human Akt-1 sequence, comprising Seq. Id. No. 4 RX-0201, 5' gctgcatgatctccttggcg 3'.

11. A compound, RX-0632, having a sequence comprising Seq. Id. No. 16 5' tggtgcagcggcagcggcag 3', targeted to a nucleic acid molecule encoding human Akt-1, wherein said oligonucleotide compound inhibits the expression of human Akt-1.

12. The compound of claim 11, wherein the compound is an antisense oligonucleotide.

13. The antisense oligonucleotide of claim 12 having at least one modified internucleoside linkage that is a phosphorothioate linkage.

14. A method of inhibiting the expression Akt-1 in human cells or tissues comprising contacting said cells or tissues with the compound of claim 11.

15. A method of inducing cytotoxicity in a cancer cell comprising the step of introducing into the cell an oligonucleotide that hybridizes to a human Akt-1 sequence, comprising, RX-0632, Seq. Id. No. 16, 5' tggtgcaucggcagcggcau 3'.

16. A compound, RX-0638, having a sequence comprising Seq. Id. No. 17 5' ggcgcgagcgcgggcctagc 3', targeted to a nucleic acid molecule encoding human Akt-1, wherein said oligonucleotide compound inhibits the expression of human Akt-1.

17. The compound of claim 16, wherein the compound is an antisense oligonucleotide.

18. The antisense oligonucleotide of claim 17 having at least one modified internucleoside linkage that is a phosphorothioate linkage.

19. A method of inhibiting the expression Akt-1 in human cells or tissues comprising contacting said cells or tissues with the compound of claim 16.

20. A method of inducing cytotoxicity in a cancer cell comprising the step of introducing into the cell an oligonucleotide that hybridizes to a human Akt-1 sequence, comprising, RX-0638, Seq. Id. No. 17, 5' ggcgcgagcgcgggcctagc 3'.

* * * * *

SEQUENCE LISTING

<160> NUMBER OF SEQ ID NOS: 22

<210> SEQ ID NO 1
<211> LENGTH: 20
<212> TYPE: DNA
<213> ORGANISM: Human

<400> SEQUENCE: 1
agtggactgg tggggctgg          20

<210> SEQ ID NO 2
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 2
ccagccccca ccagtccact                                               20

<210> SEQ ID NO 3
<211> LENGTH: 20
<212> TYPE: DNA
<213> ORGANISM: Human

<400> SEQUENCE: 3
cgccaaggag atcatgcagc                                               20

<210> SEQ ID NO 4
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 4
gctgcatgat ctccttggcg                                               20

<210> SEQ ID NO 5
<211> LENGTH: 19
<212> TYPE: DNA
<213> ORGANISM: Artificial Sequence
<220> FEATURE:
<223> OTHER INFORMATION: PCR Primer

<400> SEQUENCE: 5
ctggacaagg acgggcaca                                                19

<210> SEQ ID NO 6
<211> LENGTH: 23
<212> TYPE: DNA
<213> ORGANISM: Artificial Sequence
<220> FEATURE:
<223> OTHER INFORMATION: PCR Primer

<400> SEQUENCE: 6
ggtgggctga gcttcttctc gta                                           23

<210> SEQ ID NO 7
<211> LENGTH: 20
<212> TYPE: DNA
<213> ORGANISM: Artificial Sequence
<220> FEATURE:
<223> OTHER INFORMATION: PCR Primer

<400> SEQUENCE: 7
cccatgccat cctgcgtctg                                               20

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
acggagtact tgcgctcag                                                19
```

<210> SEQ ID NO 9
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 9
ggtgcttggg cttggccagg                                               20

<210> SEQ ID NO 10
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 10
ctgagggctg aggccacacc                                               20

<210> SEQ ID NO 11
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 11
gtgccgcaaa aggtcttc                                                 18

<210> SEQ ID NO 12
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 12
gcctctccat ccctccaa                                                 18

<210> SEQ ID NO 13
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 13
agatagctgg tgacagacag                                               20

<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14
cgtggagaga tcatctgagg                                               20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 15
tcgaaaaggt caagtgctac                                               20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
tggtgcagcg gcagcggcag                                               20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
ggcgcgagcg cgggcctagc                                               20

<210> SEQ ID NO 18
<211> LENGTH: 20
<212> TYPE: DNA
<213> ORGANISM: Human

<400> SEQUENCE: 18
ctgtctgtca ccagctatct                                               20

<210> SEQ ID NO 19
<211> LENGTH: 20
<212> TYPE: DNA
<213> ORGANISM: Human

<400> SEQUENCE: 19
cctcagatga tctctccacg                                               20

<210> SEQ ID NO 20
<211> LENGTH: 20
<212> TYPE: DNA
<213> ORGANISM: Human

<400> SEQUENCE: 20
gtagcacttg accttttcga                                               20

<210> SEQ ID NO 21
<211> LENGTH: 20
<212> TYPE: DNA
<213> ORGANISM: Human

<400> SEQUENCE: 21
ctgccgctgc cgctgcacca                                               20

<210> SEQ ID NO 22
<211> LENGTH: 20
<212> TYPE: DNA
<213> ORGANISM: Human

<400> SEQUENCE: 22
gctaggcccg cgctcgcgcc                                               20
```